(12) United States Patent
Agrawal et al.

(10) Patent No.: US 10,817,832 B1
(45) Date of Patent: Oct. 27, 2020

(54) AUTOMATED REPLENISHMENT SYSTEM FOR PERSONAL MEDICAL KITS

(71) Applicants: Akhil K. Agrawal, Davie, FL (US); Sukrit Agrawal, Miami, FL (US)

(72) Inventors: Akhil K. Agrawal, Davie, FL (US); Sukrit Agrawal, Miami, FL (US)

( * ) Notice: Subject to any disclaimer, the term of this patent is extended or adjusted under 35 U.S.C. 154(b) by 739 days.

(21) Appl. No.: 15/172,375

(22) Filed: Jun. 3, 2016

(51) Int. Cl.
  *G06Q 10/08* (2012.01)
  *G06Q 20/20* (2012.01)
  *G06Q 30/06* (2012.01)
  *A61M 16/18* (2006.01)

(52) U.S. Cl.
  CPC ......... *G06Q 10/087* (2013.01); *A61M 16/183* (2013.01); *G06Q 20/203* (2013.01); *G06Q 30/0601* (2013.01); *A61J 2205/60* (2013.01)

(58) Field of Classification Search
  CPC .............. G06Q 10/087; G06Q 20/203; G06Q 30/0601; A61M 16/183
  USPC ...... 705/22, 23, 28, 333, 338; 700/214, 237, 700/241; 340/10.1; 604/385, 492
  See application file for complete search history.

(56) References Cited

U.S. PATENT DOCUMENTS

| | | | | |
|---|---|---|---|---|
| 2008/0316045 | A1* | 12/2008 | Sriharto | G06Q 50/22 340/10.1 |
| 2013/0173287 | A1* | 7/2013 | Cashman | E04H 3/08 705/2 |
| 2014/0337040 | A1* | 11/2014 | Debusk | G06Q 10/087 705/2 |
| 2016/0085922 | A1* | 3/2016 | Sweeney | A61B 90/90 705/2 |
| 2016/0210439 | A1* | 7/2016 | Hartlaub | G06F 19/3462 |
| 2016/0210481 | A1* | 7/2016 | Hussain | G06K 7/10178 |

* cited by examiner

*Primary Examiner* — Vanel Frenel
(74) *Attorney, Agent, or Firm* — Patents on Demand P.A.; Brian K. Buckheit (57) ABSTRACT

The MedicSMART system can be a replenishment system for personal medical kits. The personal medical kit can house an inventory of personal use medical supplies within a container that is in a location personally associated with a user. Each medical supply can have a radio-frequency identification (RFID) tag affixed thereon. The payment artifact can be used for the user's electronic transactions. The MedicSMART system can be configured to automatically replenish the inventory of the personal medical kit using a client device, supply thresholds, supplier data, and a server. The client device can be installed within the container to collect data from the RFID tags. The supply thresholds can define minimum values for the medical supplies. The supplier data can define suppliers for purchasing the medical supplies. The server can be configured to automatically order medical supplies to maintain the personal medical kit in an acceptable state.

17 Claims, 4 Drawing Sheets

AUTOMATED REPLENISHMENT SYSTEM FOR PERSONAL MEDICAL KITS

BACKGROUND

The present invention relates to the field of remote monitoring and, more particularly, to an automated replenishment system for personal medical kits.

Many people, both singles and families, often keep a medical kit for use in a personal location like their home or car. However, managing the inventory of medical supplies contained in these personal medical kits is still a manual operation, which is often overlooked.

Further, many people utilize a variety of medical supplies for home treatment of chronic conditions. In such cases, it is easy to not realize that the amount of medical supplies needs to be replenished until it is exhausted. This often causes additional stress and cost (i.e., rush shipping charges) to restock their personal medical kit.

What is needed is a solution that automatically monitors the inventory levels of medical supplies in a personal medical kit. Such a solution should be capable of ordering medical supplies to maintain the inventory of the personal medical kit at predefined levels.

BRIEF SUMMARY

One aspect of the present invention can include a medical kit replenishment system comprised of a personal medical kit, a payment artifact, and a MedicSMART system. The personal medical kit can house an inventory of medical supplies within a container. The inventory of medical supplies can be suitable for personal use. Each medical supply can have a radio-frequency identification (RFID) tag affixed thereon. The RFID tag can store data regarding the medical supply to which it is affixed. The personal medical kit can be situated within a location personally associated with a user of the personal medical kit. The payment artifact can be associated with the user and can be used for electronic transactions. The MedicSMART system can be external to the location personally associated with the user and can be configured to automatically replenish the inventory of the personal medical kit. The MedicSMART system can include a client device, supply thresholds, supplier data, and a server. The client device can be installed within the container and can be configured to collect data from the RFID tags. The client device can be capable of wireless communications. The supply thresholds can define minimum values for each type of medical supply in the personal medical kit. The supplier data can be provided by the user and can define suppliers for purchasing the medical supplies of the personal medical kit. The server can be remotely-located from the client device and can be configured to automatically order medical supplies to maintain the personal medical kit in an acceptable state using the RFID tag data received from the client device, the supply thresholds, the supplier data, and the payment artifact.

Another aspect of the present invention can include a medical kit replenishment system comprised of a personal medical kit, a payment artifact, and a MedicSMART system. The personal medical kit can house an inventory of medical supplies within a container. The inventory of medical supplies can be suitable for personal use. Each medical supply can have a radio-frequency identification (RFID) tag affixed thereon. The RFID tag can store data regarding the medical supply to which it is affixed. The personal medical kit can be situated within a location personally associated with a user of the personal medical kit. The payment artifact can be associated with the user and can be used for electronic transactions. The MedicSMART system can be installed within the container and can be configured to monitor the inventory of the personal medical kit using the RFID tags. The MedicSMART system can automatically order medical supplies to replenish medical supplies that have expired or been consumed on behalf of the user using the payment artifact.

Yet another aspect of the present invention can include a method that begins with the user registering a personal medical kit and a payment artifact with a MedicSMART system. The personal medical kit can have a device of the MedicSMART system installed therein. The personal medical kit can be situated within a location personally associated with the user. Inventory values for medical supplies contained within the personal medical kit can be determined by the MedicSMART system. Each medical supply can have a radio-frequency identification (RFID) tag affixed thereon that stores data regarding the medical supply. The determined inventory values can be compared to supply thresholds. The supply thresholds can define minimum values for each type of medical supply in the personal medical kit inventory. When at least one medical supply has a determined inventory value that is below its corresponding supply threshold, medical supplies can be ordered from a user-designated supplier using the registered payment artifact. The order can be delivered to the user at the location.

DETAILED DESCRIPTION

The present invention discloses a solution for replenishing the medical supplies of a personal medical kit. The MedicSMART system can be installed in a personal medical kit. The medical supplies can be labeled with properly-configured RFID tags. The MedicSMART system can determine the current inventory of the medical supplies using the RFID tags. When the inventory drops below predefined supply thresholds, the MedicSMART system can take automatically order medical supplies to replenish the personal medical kit.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1:
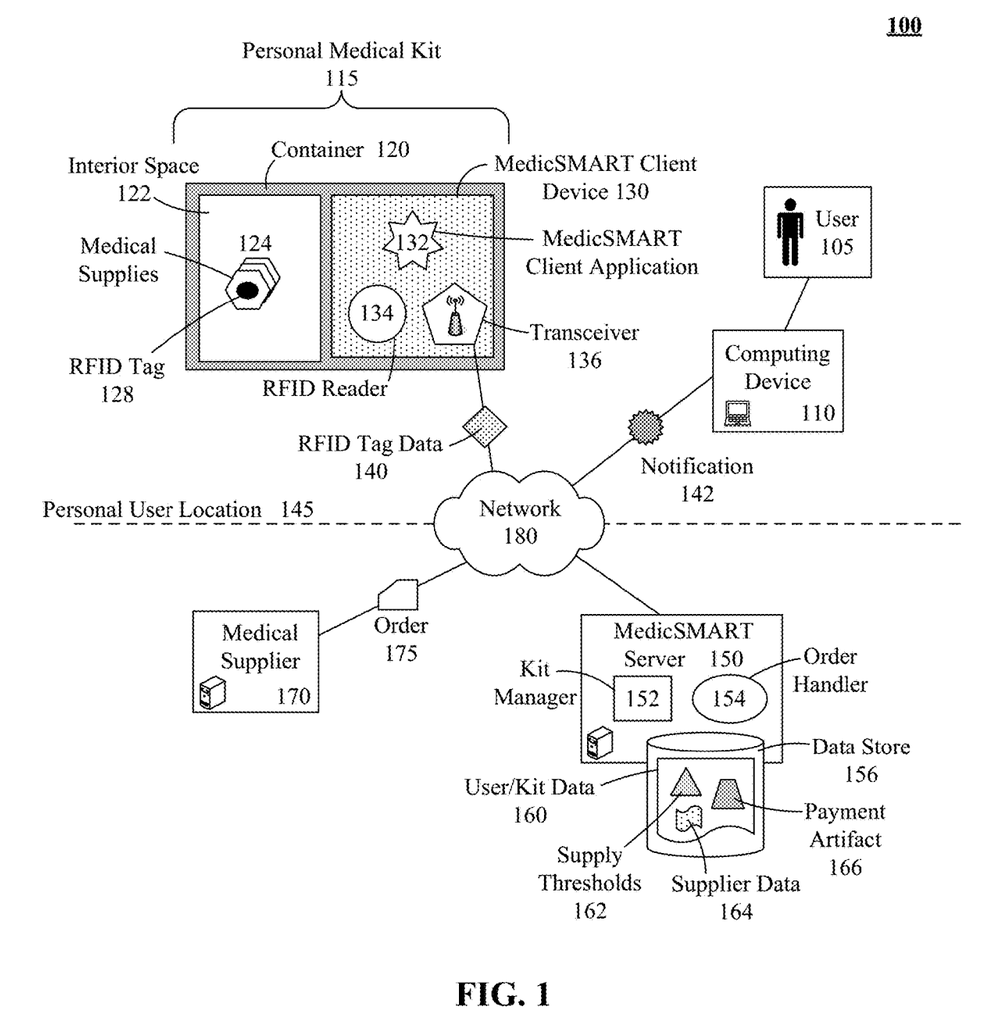
FIG. 1 is a block diagram illustrating a system that replenishes the medical supplies of a personal medical kit in accordance with embodiments of the inventive arrangements disclosed herein.

FIG. 1 is a block diagram illustrating a system 100 that replenishes the medical supplies 124 of a personal medical kit 115 in accordance with embodiments of the inventive arrangements disclosed herein. System 100 can exemplify a client-server embodiment of a MedicSMART system.

In system 100, a personal medical kit 115 having a MedicSMART client device 130 can exist at a personal user location 145. The term "personal user location" can be used to refer to a location that is personally associated with the user 105; not a public location that the user 105 happens to frequent. The geographic location of the personal user location 145 can be static like a building or mobile like a car. Examples of the personal user location 145 can include, but are not limited to, a vehicle, a house, an apartment, the user 105, a recreational vehicle, and the like.

The personal user location 145 can be owned by a separate entity and rented by the user 105 for a predefined time period like a rental car or hotel room. The personal medical kit 115 can be in the personal user location 145 in addition to any other medical kits provided by other entities.

In another embodiment, the personal medical kit 115 can be carried by the user 105 in a public venue like a museum. In such an embodiment, the personal user location 145 can be the location of the user 105 within the public venue.

The personal medical kit 115 can be a container 120 having an interior space 122 that houses medical supplies 124. The container 120 can be designed in various shapes, sizes, and/or materials.

For example, the container 120 can be a backpack made from a durable water-resistant material that can be carried around the location 145 by the user 105. As another example, the container 120 can be a rigid case that is installed at a stationary point within the user's 105 home 145.

A medical supply 124 can represent a first aid item suitable for personal use in minor health crises. Medical supplies 124 can be consumable or usable only once like an ice pack, pair of latex gloves, bandage, or alcohol wipe. Further, the medical supplies 124 can include reusable medical devices that measure and/or provide a medical service. Examples of a medical device can include, but are not limited to, an automated external defibrillator (AED), a blood pressure cuff, a glucometer, a thermometer, tweezers, shears, and the like.

Each medical supply 124 can have a radio-frequency identification (RFID) tag 128 affixed to it. The RFID tag 128 can store pertinent information about the item to which it is affixed, such as the name of the medical supply 124 and its expiration date. The RFID tag 128 can be passive and designed for use in the near-field (less than one meter) to minimize stray readings. The RFID tags 128 can utilize a variety of technology as taught in the Art.

In another contemplated embodiment, the personal medical kit 115 can be of a size for a small workplace environment.

The MedicSMART system can monitor and replenish the inventory of medical supplies 124 and/or their sub-components with minimal user 105 intervention. In system 100, the MedicSMART system can be comprised of the MedicSMART client device 130 and the MedicSMART server 150.

The MedicSMART client device 130 can be an electronic device configured to perform tasks of the MedicSMART system local to the personal medical kit 115. The MedicSMART client device 130 can be attached to or embedded within the container 120. Depending upon the specific implementation, the MedicSMART client device 130 can also be made accessible to a user 105, such as in a resealable pocket, or inaccessible to the user 105 but accessible to a technician.

The MedicSMART client device 130 can include the hardware and/or software necessary to perform its tasks including a MedicSMART client application 132, an RFID reader 134, a transceiver 136, and the like. Additional components (e.g., input/output elements, a GPS module, a digital camera, etc.) can be included in the MedicSMART client device 130 without departing from the spirit of the present invention.

In another embodiment, the MedicSMART client device 130 can have a display that is viewable through a void in a corresponding surface of the container 120; such a void can be covered with a transparent or semi-transparent protective material.

The MedicSMART client application 132 can be a software program that controls operation of the MedicSMART client device 130. The RFID reader 134 can be used to interrogate the RFID tags 128 of the medical kit's 115 inventory (medical supplies 124 and medical devices 126). The MedicSMART client device 130 should be positioned in the container 120 in such a manner to provide the RFID reader 134 full coverage of the interior space 122. The specifications of the RFID reader 134 can allow for the RFID tags 128 in the interior space 122 to be read without interfering with other electronic equipment or reading RFID tags 128 that are not part of the personal medical kit 115.

The transceiver 136 can represent the means by which the MedicSMART client device 130 wirelessly communicates with the MedicSMART server 150 and/or the user's 105 computing device 110. Multiple transceivers 136 can be required to allow the use of different types of wireless communications networks 180 and/or protocols.

In another contemplated embodiment, the MedicSMART client device 130 can include ports for a hard-wired connection to the network 180, using the transceiver 136 only for communication with the hard-wired connection is unavailable.

The RFID tag data 140 can be collected by the MedicSMART client application 132 and conveyed to the MedicSMART server 150 over the network 180. Collection of the RFID tag data 140 by the MedicSMART client application 132 can vary based on the specific implementation.

For example, the MedicSMART client application 132 can be configured to collect the RFID tag data 140 according to a predefined time interval (e.g., every week, every day, twice a month, etc.).

In another contemplated embodiment, collection of the RFID tag data 140 can be triggered by the opening/closing of a door or flap of the container 120. Such an embodiment can require the installation of additional sensors on the door/flap and connection to the MedicSMART client device 130. The MedicSMART client device 130 can require additional configuration to handle the sensor input.

The MedicSMART server 150 can represent the hardware and/or software necessary to process and respond to the RFID tag data 140 received from the MedicSMART client device 130. The MedicSMART server 150 can include a kit manager 152, an order handler 154, a data store 156 for storing user/kit data 160, and the like.

The kit manager 152 can represent the main processing functionality of the MedicSMART server 150. The kit manager 152 can process the RFID tag data 140 received from a MedicSMART client device 130 using the necessary user/kit data 160 to determine the current state of the medical supplies 124 in the personal medical kit 115.

The user/kit data 160 can be a collection of user 105 provided information for use by the MedicSMART server 150. Definition of the user/kit data 160 can utilize a user interface (not shown) that is accessible by the user 105 on a computing device 110, as is common in the Art. The user/kit data 160 can include supply thresholds 162, supplier data 164, and payment artifact 166 data.

The supply thresholds 162 can define the minimum acceptable values for each medical supply 124 in the personal medical kit 115. Default minimum values can be included that conform to an accepted standard until configured by the user 105. Alternately, the user 105 can be provided with the ability to select a standard to use that automatically sets the minimum values in accordance with the selected standard.

The supplier data 164 can represent the information necessary to place an order 175 for medical supplies 124 with a medical supplier 170. For example, the supplier data 164 can list the name, online ordering requirements, physical address, and/or email address for each medical supplier 170. The order 175 can require inclusion of the payment artifact 166 to be processed.

In an embodiment having medical supplies 124 that include a medical device having replaceable and/or disposable sub-components, the user/kit data 160 can list the sub-components that require monitoring. In such an embodiment, the sub-components can each include a separate RFID tag 128 in order to be monitored separate from the medical device 124.

The payment artifact 166 can be a means for electronically providing payment to the medical supplier 170 for the order 175. The payment artifact 166 can represent the information necessary to bill the user's 105 account with a financial institution or payment system. Examples of the payment artifact 166 can include, but are not limited to, a credit card account, a savings account, a checking account, a money market account, a digital currency account (e.g., BITCOIN), and an online payment system (e.g., PAYPAL).

Once the kit manager 152 compares the current inventory values of the medical supplies 124 contained in the RFID tag data 140 to the supply thresholds 162 and medical supply 124 expiration dates to the current date, the kit manager 152 can then determine what actions to take, if any. Allowed or preferred actions can also be defined in the user/kit data 160.

For example, if only one medical supply 124 is below its supply threshold 162, the user/kit data 160 can indicate to only provide the user 105 with a notification 142. However, if more than one medical supply 124 is below its supply threshold 162, the user/kit data 160 can instruct the kit manager 152 to immediately place an order 175 with the appropriate medical supplier 170.

As another example, the kit manager 152 can provide the user 105 with a monthly notification 142 that lists the medical supplies 124 that are close to their expiration date.

Notifications 142 can conform to a variety of electronic communication formats/standards and can be viewed by the user 105 using a suitable computing device 110. The computing device 110 can represent the hardware and/or software components that support the receipt of the notification 142 over the network 180 and presentation of the notification 142 to the user 105.

For example, the user 105 can specify receiving critical notifications 142 as text messages sent to a smartphone 110 and other notifications 142 sent as email messages to be read on a laptop computer 110.

The kit manager 152 can utilize the order handler 154 to generate orders 175 using the necessary information from the RFID tag data 140, user/kit data 160, supplier data 164, and/or payment artifact 166. The order handler 154 can electronically submit the orders 175 to the medical supplier 170. The quantity of a medical supply 124 ordered can be automatically calculated by the kit manager 152 (i.e., an amount that returns the inventory value of the medical supply 124 to its supply threshold 162) and/or defined by the user 105 (i.e., always order five).

The kit manager 152 can be further configured to archive received RFID tag data 140, notifications 142, and/or orders 175 in a data store 156 for accountability In another contemplated embodiment, the functionality of the MedicSMART server 150 can be integrated into the MedicSMART client device 130.

As used herein, presented data store 156 can be a physical or virtual storage space configured to store digital information. Data store 156 can be physically implemented within any type of hardware including, but not limited to, a magnetic disk, an optical disk, a semiconductor memory, a digitally encoded plastic memory, a holographic memory, or any other recording medium. Data store 156 can be a stand-alone storage unit as well as a storage unit formed from a plurality of physical devices. Additionally, information can be stored within data store 156 in a variety of manners. For example, information can be stored within a database structure or can be stored within one or more files of a file storage system, where each file may or may not be indexed for information searching purposes. Further, data store 156 can utilize one or more encryption mechanisms to protect stored information from unauthorized access.

Network 180 can include any hardware/software/and firmware necessary to convey data encoded within carrier waves. Data can be contained within analog or digital signals and conveyed though data or voice channels. Network 180 can include local components and data pathways necessary for communications to be exchanged among computing device components and between integrated device components and peripheral devices. Network 180 can also include network equipment, such as routers, data lines, hubs, and intermediary servers which together form a data network, such as the Internet. Network 180 can also include circuit-based communication components and mobile communication components, such as telephony switches, modems, cellular communication towers, and the like. Network 180 can include line based and/or wireless communication pathways.

Figure 2:
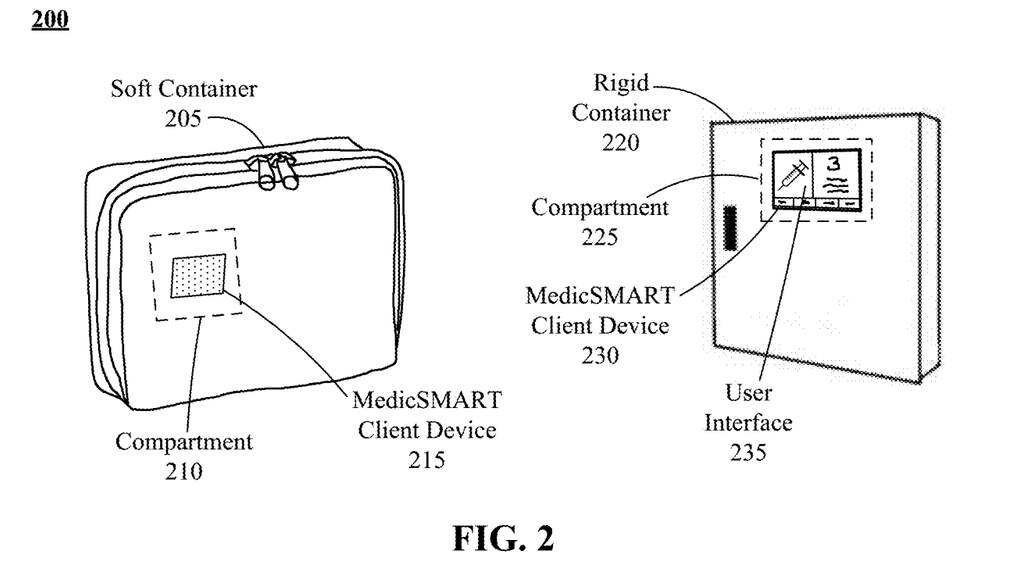
FIG. 2 depicts an illustration of example personal medical kits having MedicSMART client devices in accordance with embodiments of the inventive arrangements disclosed herein.

FIG. 2 depicts an illustration 200 of example personal medical kits having MedicSMART client devices 215 and 230 in accordance with embodiments of the inventive arrangements disclosed herein. The medical kits of illustration 200 can be utilized within the context of system 100.

Illustration 200 can present a medical kit that uses a soft container 205 and one that uses a rigid container 220. Both types of containers 205 and 220 can be similar to those currently commercially available.

The soft container 205 can be designed similar to a purse or messenger bag with one or more zippered pockets or compartments. In this example, the front pouch of the soft container 205 can include a compartment 210 for holding the MedicSMART client device 215. The compartment 210 can be attached to an interior surface of the zippered flap or lid. Alternately, the compartment 210 can exist within the space between interior and exterior layers of the flap/lid.

In this example, the user cannot directly interact with the MedicSMART client device 215. The compartment 210 can still have an open/closure means to allow a technician to service the MedicSMART client device 215.

The rigid container 220 can be similar to a medicine cabinet and can be permanently attached to a wall or other structural component. As with the soft container 205, a compartment 225 can be installed upon or within the rigid container 220 to hold the MedicSMART client device 230. In this example, a portion of the rigid container 220 can be removed to allow the user to view/use a user interface 235 for the MedicSMART client application.

It should be noted that the MedicSMART client devices 215 and 230 can be placed in other locations on or in the containers 205 and 220.

Figure 3:
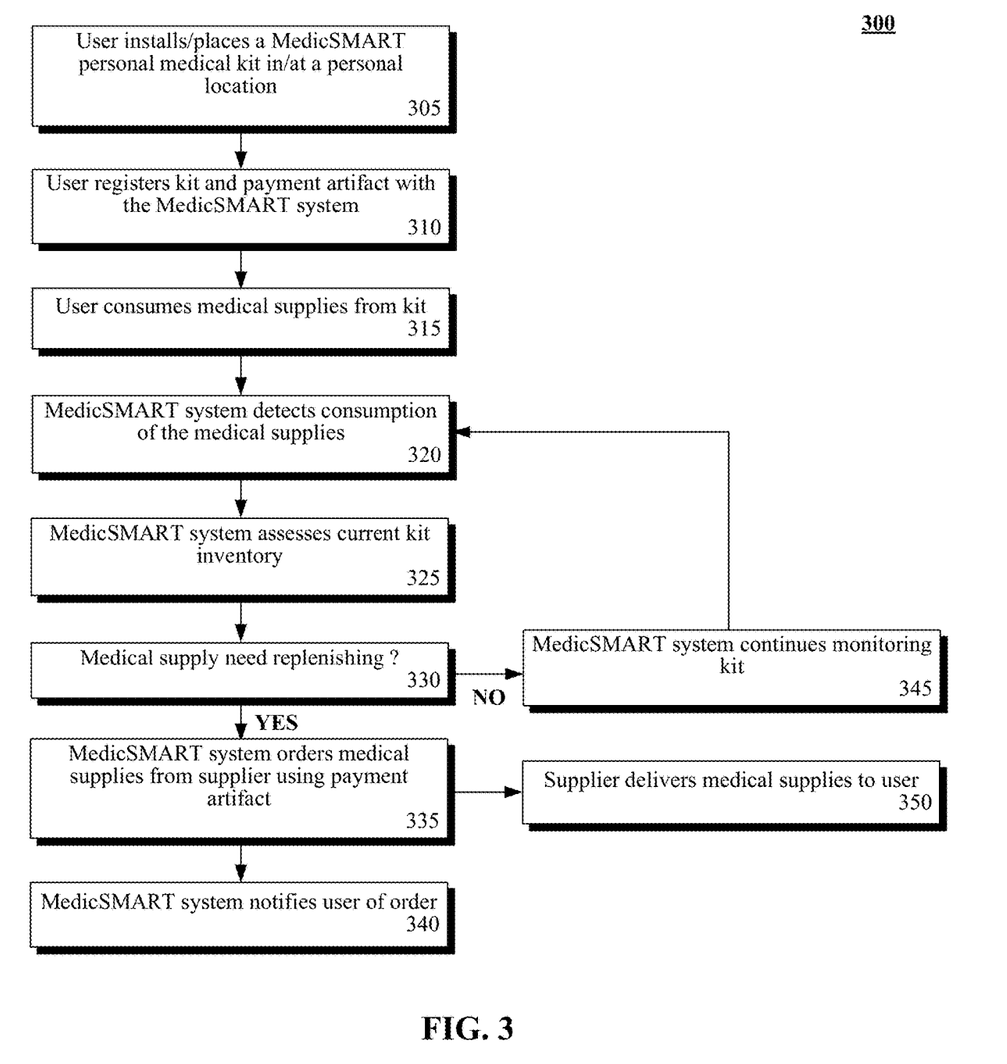
FIG. 3 is a flowchart of a method describing an example usage of the MedicSMART system with a personal medical kit in accordance with embodiments of the inventive arrangements disclosed herein.

FIG. 3 is a flowchart of a method 300 describing an example usage of the MedicSMART system with a personal medical kit in accordance with embodiments of the inventive arrangements disclosed herein. Method 300 can be performed within the context of system 300 and/or utilizing the examples of illustration 200.

Method 300 can begin in step 305 where the user installs or places a personal medical kit outfitted with the MedicSMART system in or at a personal location. The user can register the personal medical kit and a payment artifact with the MedicSMART system in step 310. In step 315, the user can consume medical supplies from the personal medical kit.

The MedicSMART system can detect the consumption of the medical supplies in step 320. Detection of medical supply consumption can be implemented in a variety of ways. For example, when the personal medical kit is a small cabinet, a sensor can be installed on the door. Opening the door can be used to mean that medical supplies are being consumed. Alternately, the MedicSMART system can be configured to assume that medical supplies are consumed over time.

In step 325, the MedicSMART system can assess the current inventory of the personal medical kit. Step 325 can require the collection and aggregation of the RFID tag data of the medical supplies. The MedicSMART system can determine if any of the medical supplies needs to be replenished (i.e., its quantity is below the supply threshold) in step 330. When the medical supplies do not need to be replenished, step 345 can execute where the MedicSMART system continues to monitor the personal medical kit. From step 345, method 300 can return to step 320.

When the medical supplies do need to be replenished, the MedicSMART system can automatically order the medical supplies from a supplier using the user's payment artifact in step 335. In step 340, the MedicSMART system can notify the user that the medical supplies have been ordered. The supplier can deliver the ordered medical supplies to the user in step 350.

It can be assumed that the user will place the delivered medical supplies in the personal medical kit. When the MedicSMART system next checks the inventory, the MedicSMART system can assess an inventory value for the medical supplies that meets or exceeds the supply thresholds. Further, the MedicSMART system can include a user-defined time frame once an order has been placed to avoid multiple orders for the same medical supply.

Figure 4:
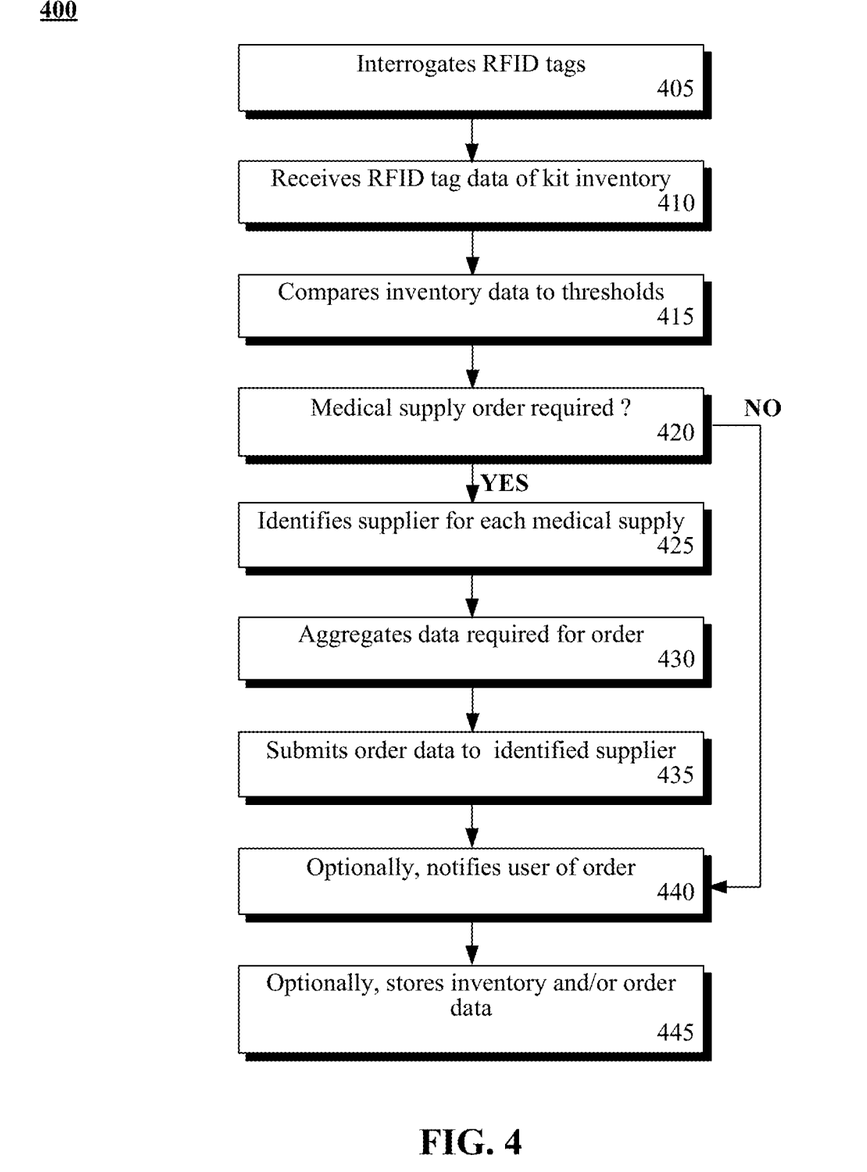
FIG. 4 is a flowchart of a method expressing the general operation of the MedicSMART system for replenishing a personal medical kit in accordance with embodiments of the inventive arrangements disclosed herein.

FIG. 4 is a flowchart of a method 400 expressing the general operation of the MedicSMART system for replenishing a personal medical kit in accordance with embodiments of the inventive arrangements disclosed herein. Method 400 can be performed within the context of system 100, illustrations 200, and/or method 300.

Method 400 can begin with step 405 where the MedicSMART system can interrogate the RFID tags of the medical supplies within the personal medical kit. The RFID tag data of the inventory of the personal medical kit can be received in step 410. In step 415, the received inventory data can be compared to the supply thresholds.

In step 420, it can be determined if an order for medical supplies is required. When an order is needed, the supplier for each medical supply to be ordered can be identified in step 425. It should be noted that, in the case of multiple and different types of medical supplies needing to be ordered, multiple suppliers can be identified in step 425.

In step 430, the data required to place the order can be aggregated, including the user's payment artifact data. The aggregated order data can be submitted to the identified supplier in step 435. Upon completion of step 435 or when an order is not needed, step 440 can be executed where the user can be, optionally, notified of the order. Optionally, the received inventory data and/or order data can be stored in step 445.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A medical kit replenishment system comprising:
a personal medical kit housing an inventory of medical supplies within a container, wherein said inventory of medical supplies is suitable for personal use, wherein each medical supply has a radio-frequency identification (RFID) tag affixed thereon, wherein the RFID tag stores data regarding a medical supply to which it is affixed, wherein the personal medical kit is situated within a location personally associated with a user of the personal medical kit;
a payment artifact associated with the user that is capable of being used for electronic transactions; and
a system, external to the location personally associated with the user, configured to automatically replenish the inventory of the personal medical kit, wherein said system comprises:
a client device installed within the container configured to collect data from the RFID tags, wherein said client device is capable of wireless communications;
a plurality of supply thresholds defining minimum values for each type of medical supply in the personal medical kit;
a plurality of supplier data, provided by the user, that defines at least one supplier for purchasing the medical supplies of the personal medical kit;
a server, remotely-located from the client device, configured to automatically order medical supplies to maintain the personal medical kit in an acceptable state using the RFID tag data received from the client device, the plurality of supply thresholds, the plurality of supplier data, and the payment artifact, wherein the server further comprises:
a kit manager configured to assess the RFID tag data for the personal medical kit using the plurality of supply thresholds to determine a current state of the medical kit and actions to execute as a result of said assessment, wherein said actions at least comprise sending a notification to the user, placing an order for at least one medical supply, and storing the received RFID tag data in a data store, wherein the notification informs the user of at least one of the current state of the personal medical kit, exceptions to supply thresholds, and the order placed on behalf of the user for the personal medical kit; and
an order handler configured to generate and convey the order to a supplier defined for the at least one medical supply in the plurality of supplier data,
wherein the personal medical kit is a first aid kit that self-monitors medical supplies via RFID tags, that automatically detects when the medical supplies fall below a supply threshold established by the user, and that automatically orders supplies from an online user-specified supplier using a credit card of the user.

2. The system of claim 1, wherein the client device further comprises:
an RFID reader configured to interrogate the RFID tags of the plurality of medical supplies within the personal medical kit to access the data stored on the RFID tags;
at least one means for communicating with the server; and
a client application configured to control operation of the client device.

3. The system of claim 2, wherein the client device further comprises:
a display for presenting data to the user; and
at least one means for receiving user-inputted data.

4. The system of claim 3, wherein the client application further comprises:
  a user interface that utilizes the display and the at least one means for receiving user-inputted data to allow the user to interact with the system.

5. The system of claim 2, wherein the client application further comprises:
  a data collection module configured to utilize the RFID reader and the at least one means for communicating to aggregate and convey the RFID tag data to the server.

6. The system of claim 1, wherein the container of the personal medical kit is one of a soft-material portable bag, a rigid material portable case, and a rigid material case permanently installed upon a structure within the location.

7. The system of claim 1, wherein the client device is enclosed within a specialized compartment of the personal medical kit container.

8. The system of claim 1, wherein the user consumes medical supplies from the personal medical kit for the user's personal use at the user's home, which is the location, and wherein the personal medical kit is a first aid item for personal use in minor health crises.

9. The system of claim 1, wherein the location is the house of the user.

10. The system of claim 1, wherein the location is a vehicle of the user.

11. The system of claim 1, wherein the personal medical kit is carried by the user in public venues.

12. The system of claim 1, wherein the personal medical kit is a first aid item for personal use in minor health crises.

13. The system of claim 1, wherein the user of the personal medical kit sets the supply thresholds.

14. The system of claim 1, wherein the payment artifact is one that bills a financial institution account of the user.

15. The system of claim 1, wherein the payment artifact is a credit card of the user that is linked to a credit card account of the user.

16. The system of claim 1, wherein the medical supplies are ones for home treatment of chronic conditions suffered by the user.

17. The system of claim 1, wherein the server automatically reorders ones of the medical supplies that have expired and that have been consumed on behalf of the user using the payment artifact.

* * * * *